United States Patent [19]
Lee et al.

[11] Patent Number: 5,296,463
[45] Date of Patent: Mar. 22, 1994

[54] COMPOSITIONS AND METHODS FOR IMPROVING COLD TOLERANCE IN ANIMALS AND HUMANS

[75] Inventors: Tze-Fun Lee; Lawrence C. H. Wang, both of Edmonton, Canada

[73] Assignee: University of Alberta, Edmonton, Canada

[21] Appl. No.: 9,995

[22] Filed: Jan. 27, 1993

Related U.S. Application Data

[60] Division of Ser. No. 700,320, May 9, 1991, Pat. No. 5,192,740, which is a continuation of Ser. No. 287,974, Dec. 20, 1988, abandoned.

[51] Int. Cl.$^5$ .................. A61K 31/00; A61K 31/70; A61K 31/715; A61K 31/52
[52] U.S. Cl. .......................................... 514/2; 514/23; 514/60; 514/263; 514/264
[58] Field of Search .................... 514/2, 23, 60, 263, 514/264

[56] References Cited

PUBLICATIONS

Ogawa, et al., Chem. Abst. 106:31620p, 1987.

*Primary Examiner*—John W. Rollins
*Attorney, Agent, or Firm*—Nixon & Vanderhye

[57] ABSTRACT

The invention disclosed is a composition for improving cold tolerance in animals and humans, comprising an adenosine receptor antagonist or an adenosine de-activator. Preferably, a nutritional supplement is also provided which further enhances cold tolerance. The nutritional supplement includes various combinations and amounts of carbohydrate, protein and fat.

11 Claims, 16 Drawing Sheets

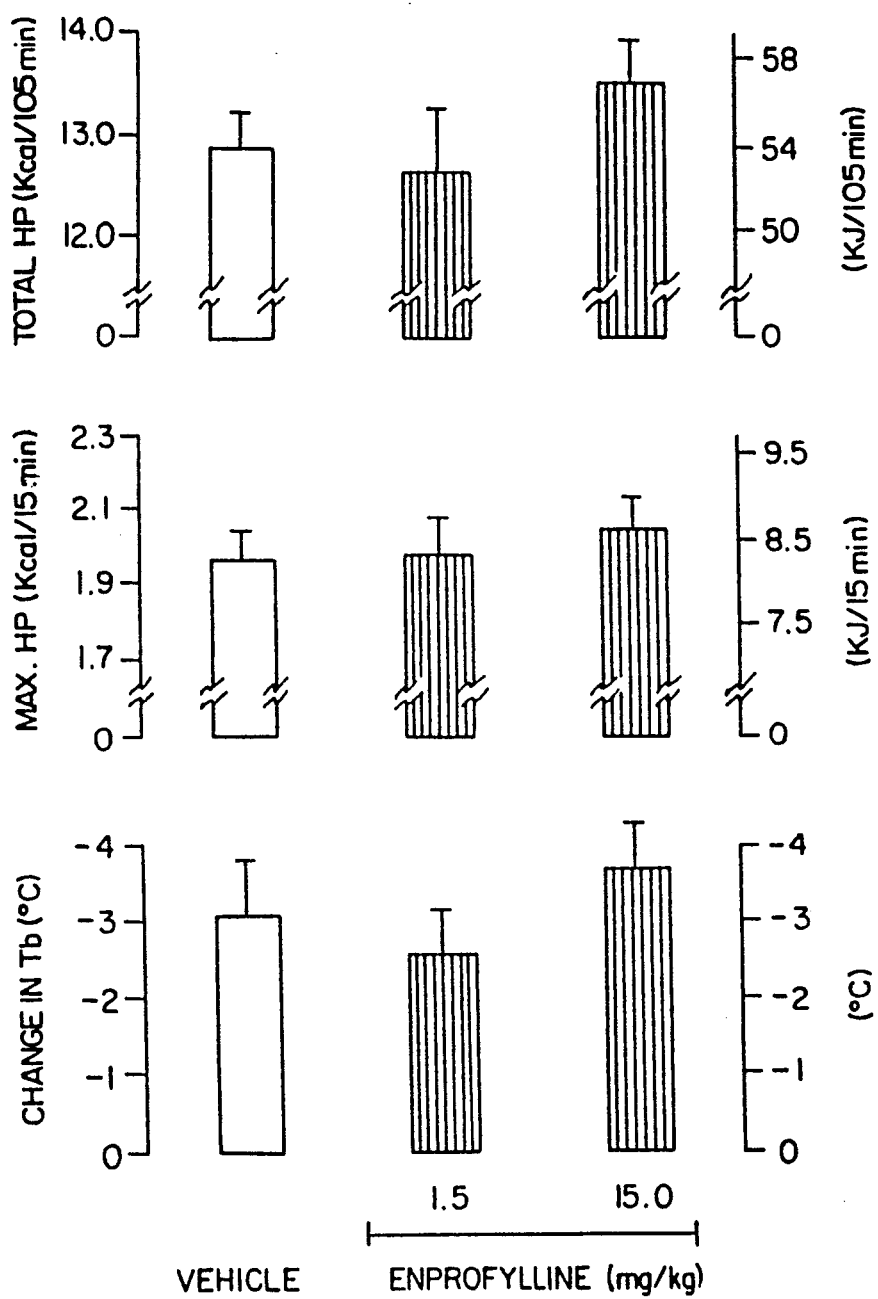

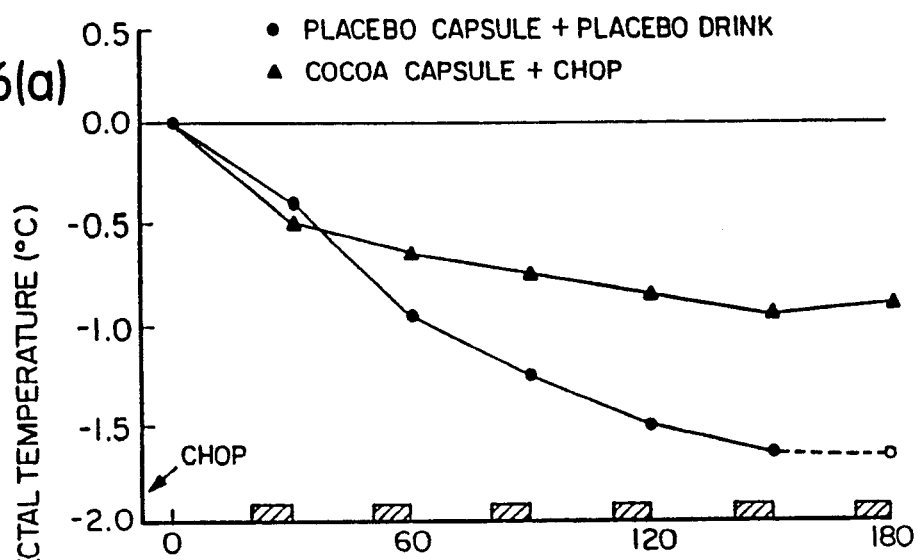
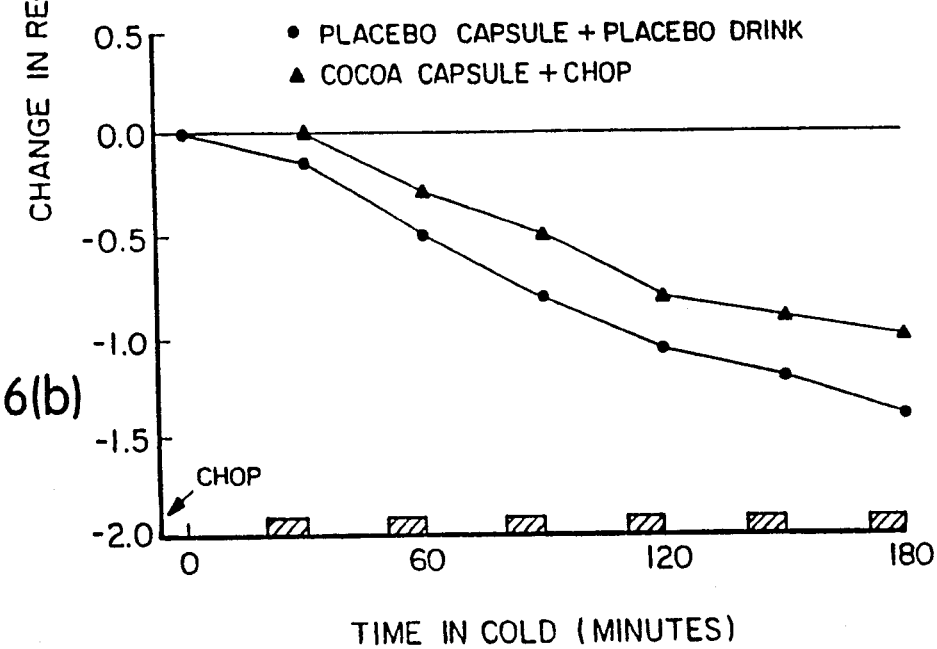

COMPOSITIONS AND METHODS FOR IMPROVING COLD TOLERANCE IN ANIMALS AND HUMANS

CROSS REFERENCE TO RELATED APPLICATIONS

This application is a division of earlier application Ser. No. 07/700,320 filed May 9, 1991, now U.S. Pat. No. 5,192,740, which in turn is a continuation of application Ser. No. 07/287,974 filed Dec. 20, 1988, abandoned.

This invention relates to improving cold tolerance and prevention of accidental hypothermia in animals and humans.

When exposed to severe cold, mammals increase their heat production to counter heat loss in order to maintain a constant body temperature. If heat loss surpasses maximum heat production, hypothermia results and unless aided by exogenous heat, death ensues. Given that defence operations and emergencies can involve prolonged cold exposure, any treatment that may enhance thermogenesis would be beneficial in reducing or eliminating the danger of becoming hypothermic.

Theophylline (THEO) and aminophylline (AMPY; 85% theophylline, 15% ethylenediamine) have been shown to elevate maximum thermogenesis and to improve cold tolerance in animals and man in severe cold. However, their mechanism of action is widely disputed. One school of thought is that competitive inhibition of phosphodiesterase (PDE) activity and thus increased levels of intracellular cAMP for enhanced substrate conversion and mobilization is responsible. Another involves competitive antagonism against adenosine receptors, thereby releasing the antilipolytic effect of adenosine after sympathetic stimulation in the cold. Since both of these known compounds are non-selective adenosine antagonists, i.e. they exhibit other pharmacological activity, the operating mechanism was uncertain.

In considering the possible role of adenosine in thermogenesis, adenosine is formed as an end product of ATP hydrolysis following physiological stimulation, e.g. adrenergic or local hypoxia. It is released into extracellular space and binds to adenosine receptors on the cell surface and exerts an inhibiting influence on substrate (fuel) mobilization. Since substrate availability is a critical limiting factor for full expression of heat producing capability in the cell, a shortage of fuel supply would lend to less than full expression of thermogenic capability and reduced cold resistance. The use of adenosine antagonists should rectify this deficiency and amplify the body's own cold fighting ability.

To test the mechanism of adenosine antagonism, a known selective adenosine receptor antagonist, 8-phenyltheophylline (8-PT) which preferentially binds to adenosine receptors was used. To test the mechanism of PDE inhibition, a selective PDE inhibitor, enprofylline (ENPRO) which is devoid of adenosine antagonism was employed.

It was also contemplated that if adenosine antagonism was established as the operating mechanism, other means for blocking the effects of adenosine could achieve the same result. Accordingly, adenosine de-activators were employed.

It was found by applicant that rats receiving ENPRO (1.5 and 15 mg/kg, i.p.) failed to show enhanced thermogenesis. In contrast, treatment with either enzyme de-activator or optimal doses of 8-PT significantly increased ($p<0.05$) thermogenesis and cold tolerance.

Having established that the operating mechanism for improved thermogenesis and cold tolerance clearly involves the competitive antagonism against adenosine receptors, according to the invention, a method for improving the cold tolerance of animals and humans is contemplated, which comprises ingesting orally or injecting into an animal or human host (a) a therapeutically effective amount of an adenosine receptor antagonist, excluding theophylline and aminophylline alone; or (b) an adenosine de-activator.

Representative adenosine receptor antagonists include xanthines of the structural formula

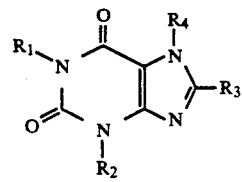

wherein $R_1$ and $R_2$ are H or lower-alkyl, $R_4$ is H or $CH_3$, and $R_3$ is

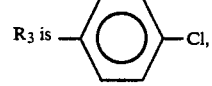

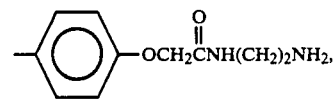

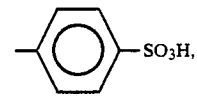

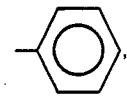

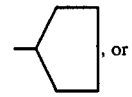, or

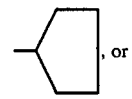

H; provided that when $R_1$ and $R_2$ are both $CH_3$, $R_3$ and $R_4$ are not both H.

Other non-xanthine adenosine antagonists such as triazoloquinazoline, pyrazoloquinoline, pyrazolopyridine and imidazopyrimidine are also contemplated.

In the drawing which illustrates the preferred embodiments of the invention:

FIGS. 9a-9c are graphs which illustrate the effect of enprofylline (ENPRO) on heat production;

Figure 15A:
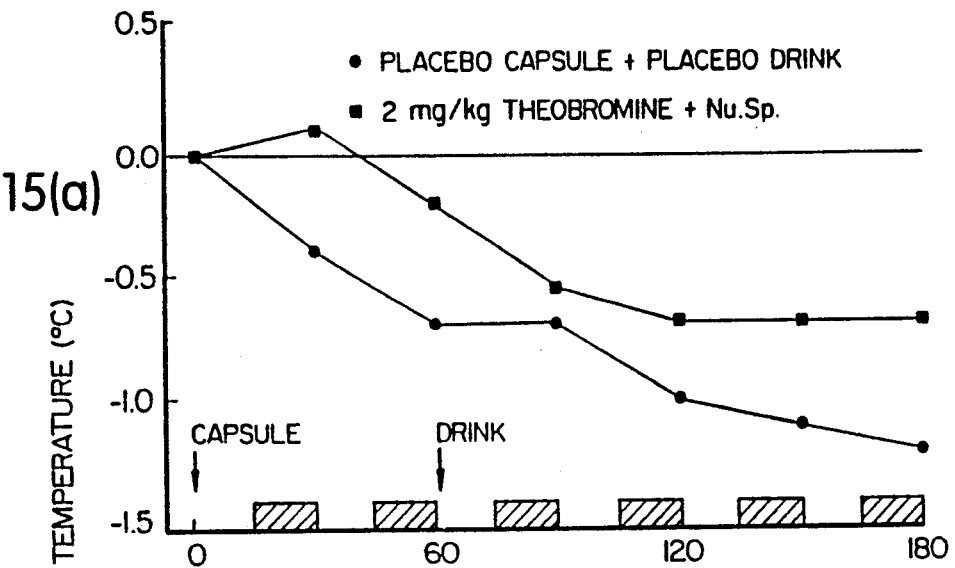
Figure 15B:
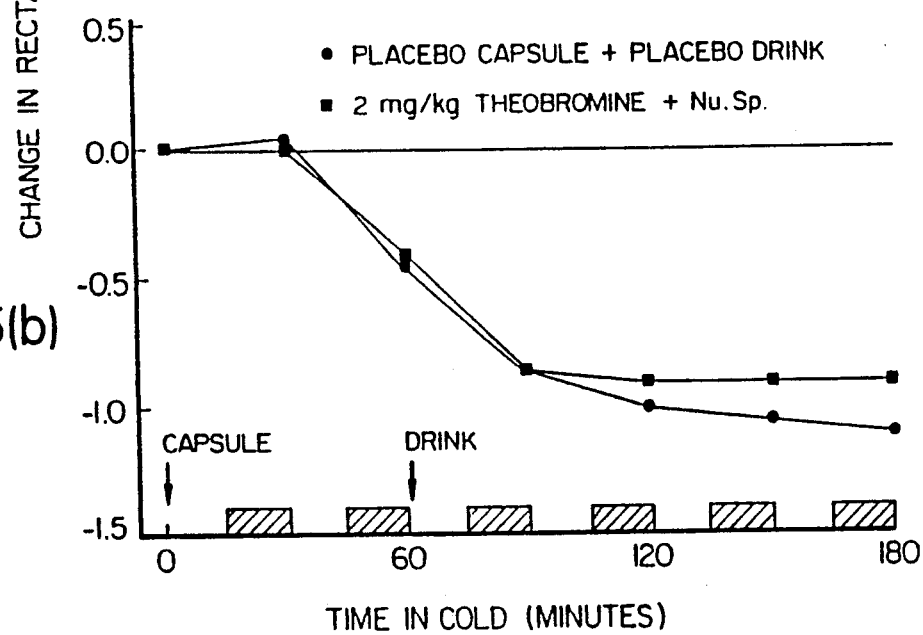

FIGS. 15a-15b are graphs which illustrate the effects of placebo treatments and theobromine (2 mg/kg p.o.) plus nutritional supplement on cold tolerance in two male subjects; experimental protocol as in Table 5; and FIGS. 16a-16b are graphs which illustrate the effects of placebo treatments and theobromine (in the form of cocoa powder containing 1.5% theobromine for an equivalent 2 mg/kg p.o.) plus nutritional supplement on cold tolerance in two subjects (one male, one female); experimental protocol as in Table 6.

EXPERIMENTAL

The following additional pure chemical compounds which are known to have adenosine antagonistic effects were tested for increased heat producing capability and hence improved cold tolerance in animals and humans:
8-cyclopentyltheophylline (CPT);
8-phenyltheophylline (8-PT);
8-(4-(2-aminoethyl)amino) carboxylmethyloxyphenyl)-1,3-dipropylxanthine (XAC);
8-(2-amino-4-chlorophenyl)-I,3-dipropylxanthine (PACPX);
8-(p-sulfophenyl)-1,3-dipropyl xanthine (DPSPX);
caffeine (1,3,7-trimethylxanthine); and
theobromine (3,7-dimethylxanthine).

CPT has the advantage of being highly soluble in water and is thus the easiest to administer by injection.

Caffeine is also easily soluble in water but its adenosine antagonistic effect is not as strong as that of CPT. Theobromine is not very soluble in water; we circumvented this problem by applying both injection and oral administration. The other compounds are dissolved in suitable organic solvents, i.e. in polyethylene glycol (8-PT)-or DMSO (XAC, PACPX and DPSPX) because of their insolubility in water. Control injections using the vehicle only are required in these cases.

Figure 1A:
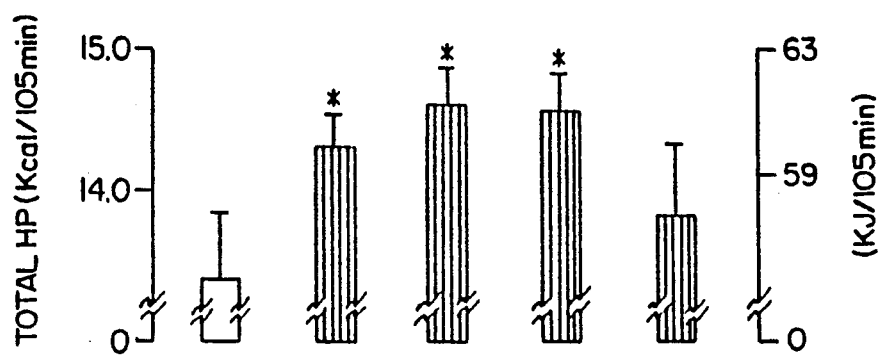
FIGS. 1a-1c are graphs which illustrate the effect of injected 8-phenyltheophylline (8-PT) on heat production.
Figure 1B:
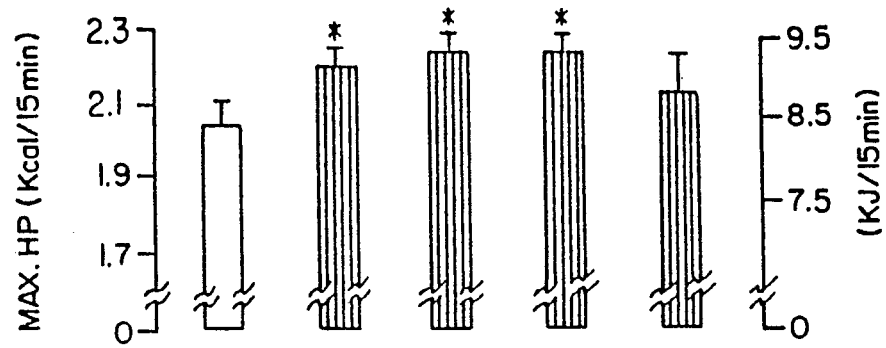
Figure 1C:
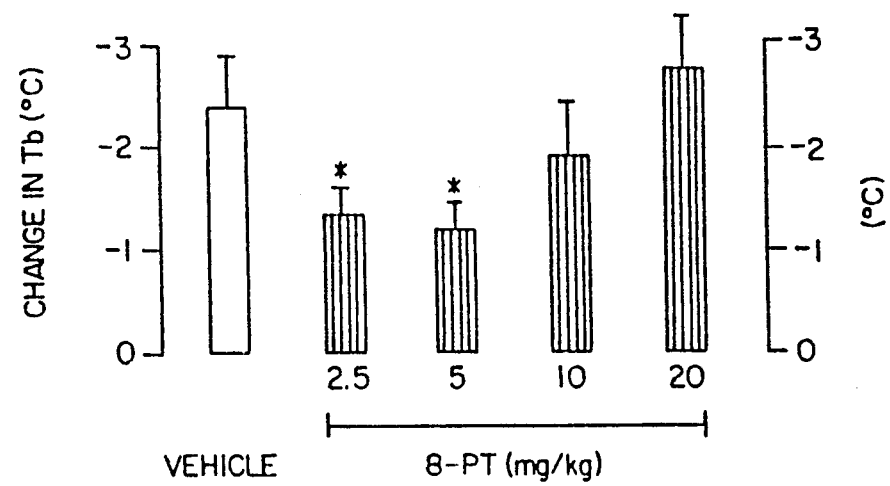
Figure 2A:
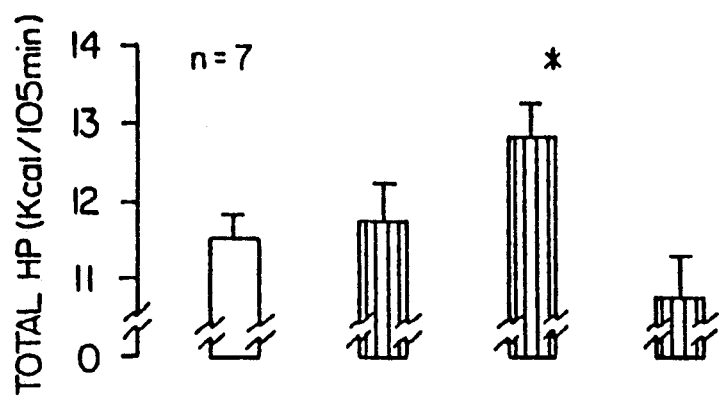
FIGS. 2a-2c are graphs which illustrate the effect of injected 8-cyclopentyltheophylline (CPT) on heat production.
Figure 2B:
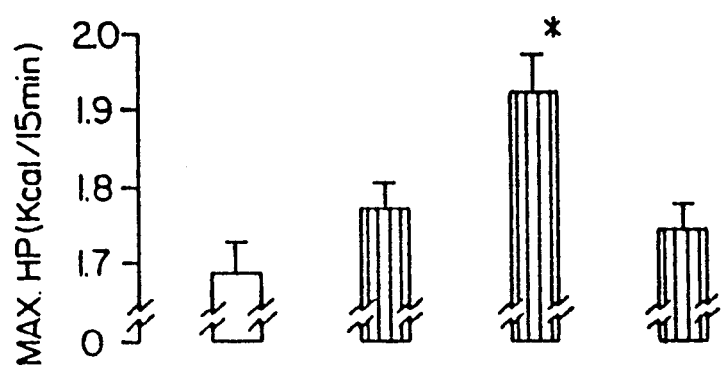
Figure 2C:
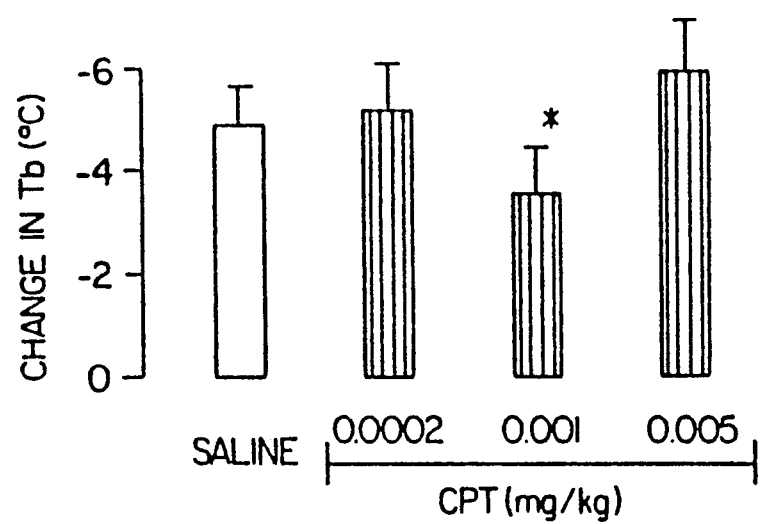
Figure 3A:
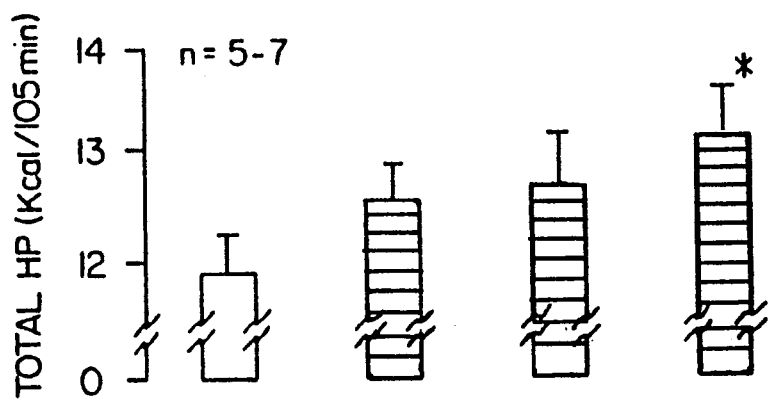
FIGS. 3a-3c are graphs which illustrate the effect of injected caffeine on heat production.
Figure 3B:
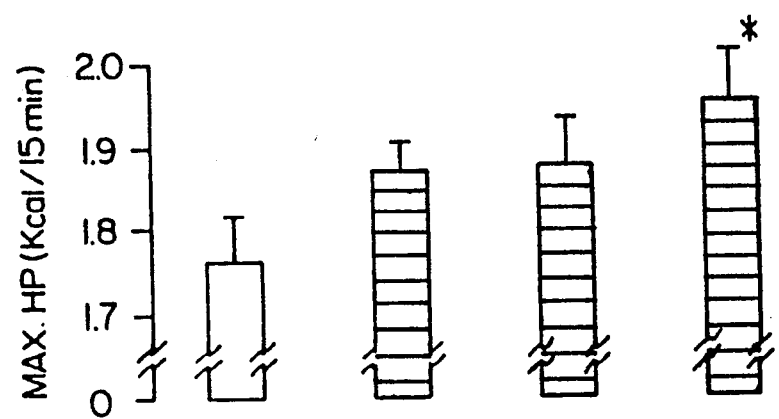
Figure 3C:
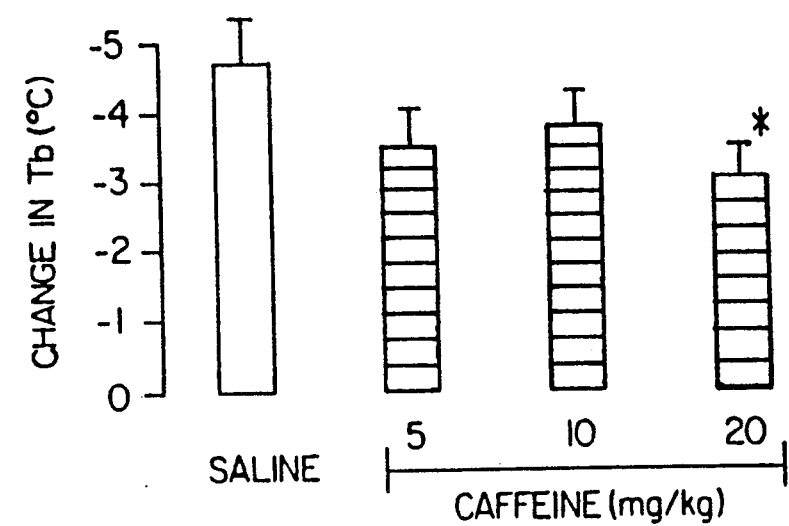
Figure 4A:
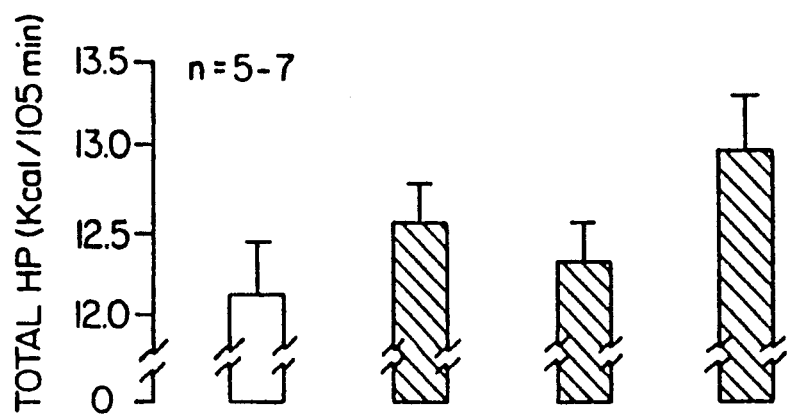
FIGS. 4a-4c are graphs which illustrate the effect of injected theobromine on heart production.
Figure 4B:
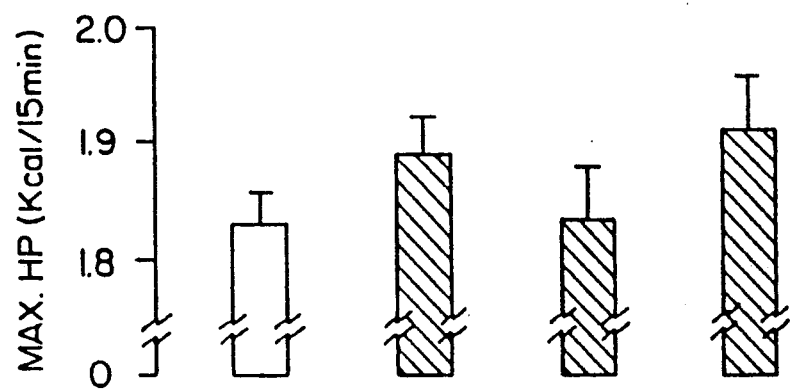
Figure 4C:
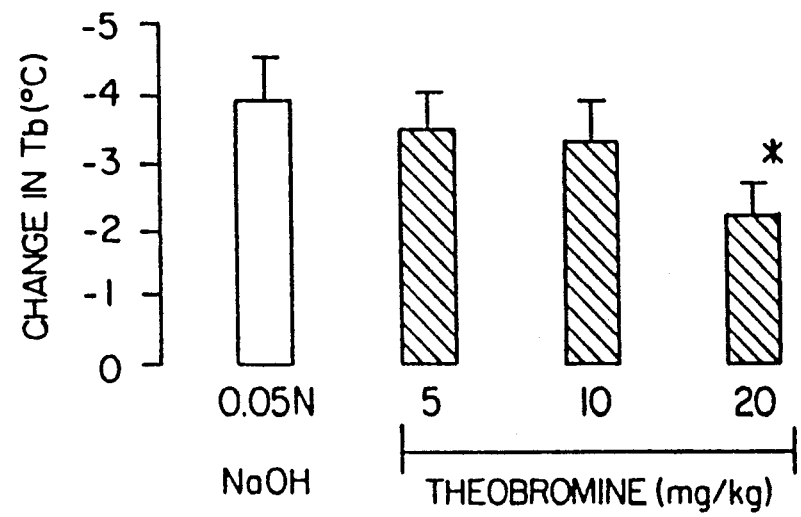
Figure 5A:
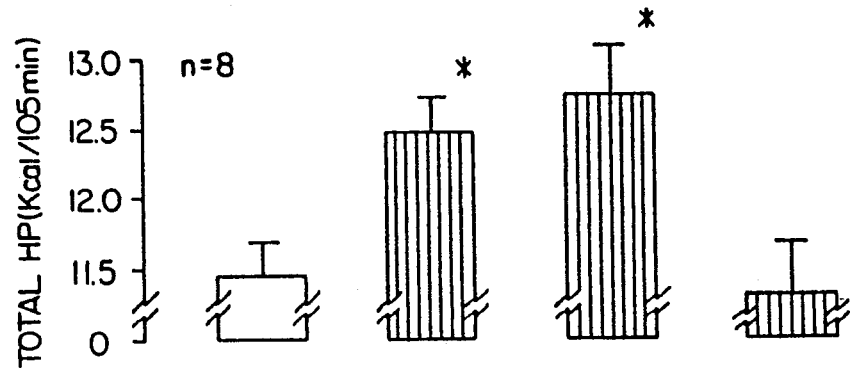
FIGS. 5a-5c are graphs which illustrate the effect of orally administered theobromine (in the form of cocoa) on heat production.
Figure 5B:
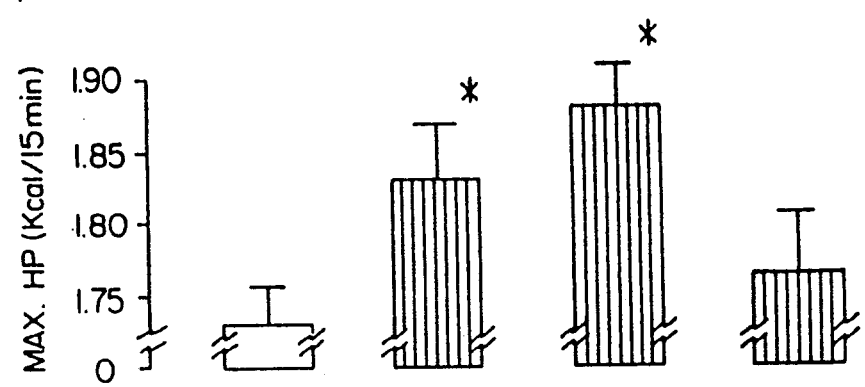
Figure 5C:
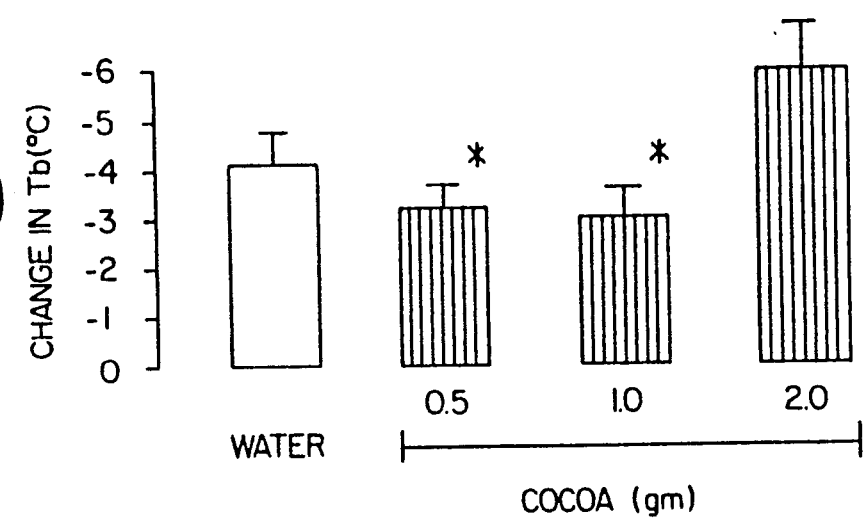
Figure 7A:
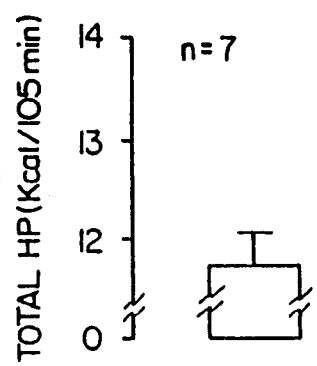
FIGS. 7a-7c are graphs which illustrate the effect of injected 8-(2-amino-4-chlorophenyl)-1,3-dipropyl xanthine (PACPX) on heat production.
Figure 7B:
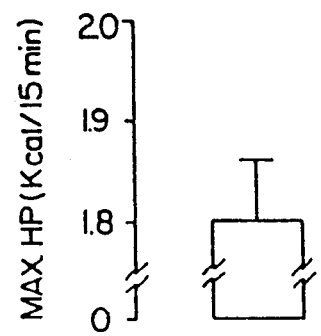
Figure 7C:
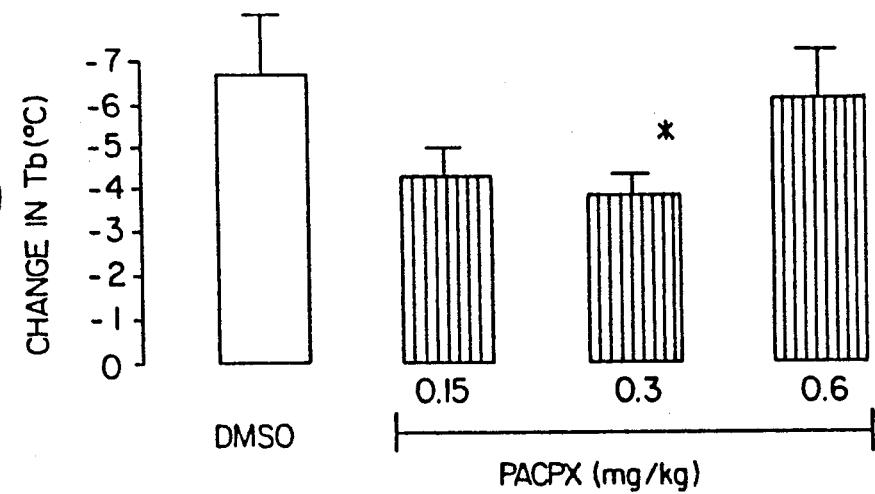
Figure 8A:
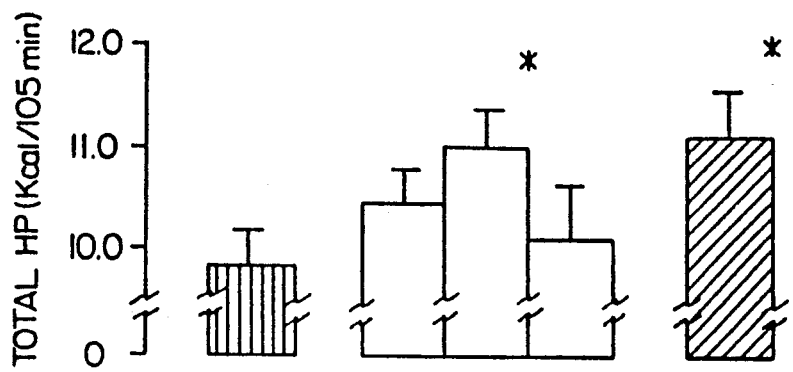
FIGS. 8a-8c are graphs which illustrate the effect of injected 8-(p-sulfophenyl)-1,3-dipropyl xanthine (DPSPX) on heat production.
Figure 8B:
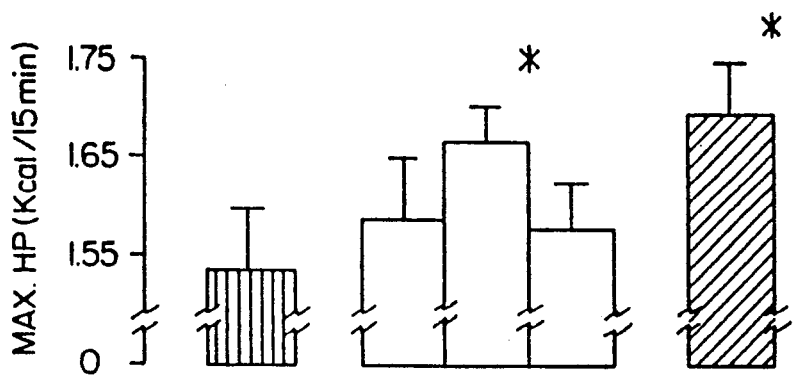
Figure 8C:
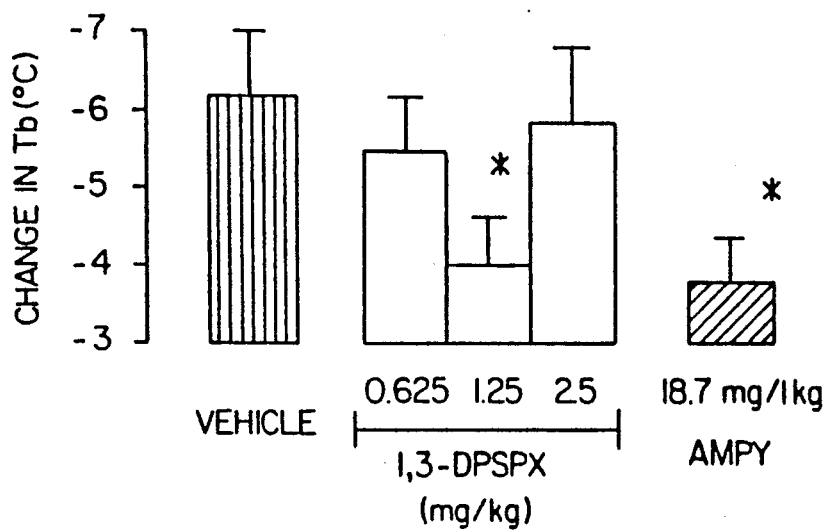

As can be seen from the results, CPT (FIGS. 2a-2c), PACPX (FIGS. 7a-7c) and DPSPX (FIGS. 8a-8c) significantly increased the heat producing capability of the rats and significantly increased their cold resistance as seen by the very much higher final body temperature after 2 hours of severe cold exposure. 8-PT also significantly increased thermogenesis and cold resistance in a dose-dependent manner (FIGS. 1a-1c). Because of the solubility problem, which presumably affects the absorption of the injected drug following its administration, the dosage difference between the CPT and 8-PT is about 5,000 fold relecting their concentrational differences in vitro receptor binding studies. Similarly, injection (i.p.) of caffeine at 20 mg/kg (FIGS. 3a-3c) and theobromine at 20 mg/kg (FIGS. 4a-4c) also demonstrated significant improvement on thermogenesis and cold resistance in the rats. Interestingly, when theobromine is administered orally to rats (FIGS. 5a-5c), significant increase in thermogenesis was also observed. Oral theobromine was administered as cocoa powder+water. This is because cocoa powder contains about 1-2% of theobromine based on dry weight with little or no other xanthine compounds present as quantified by our HPLC analysis and as indicated in the open literature (e.g. Shively and Tarka, Jr., 1984, In: The Methylxanthine Beverages and Foods: Chemistry, Consumption and Health Effects, edited by G. A. Spiller, New York: Allan Liss, p. 149-178). This indicates that through the oral route, even relatively water insoluble adenosine antagonists, such as theobromine may be quite useful as an agent for the stimulation thermogenesis and improvement of cold resistance. This has been verified in our initial studies in humans (FIGS. 12 to 16).

Figure 6A:
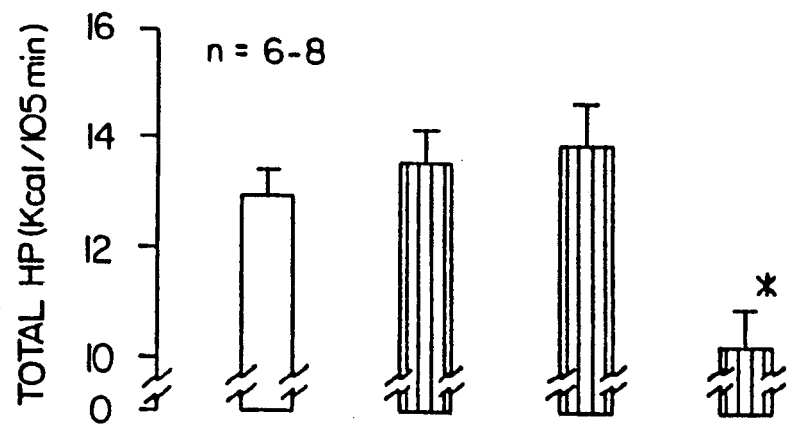
FIGS. 6a-6c are graphs which illustrate the effect of injected 8-(4-(2-aminoethyl)amino) carboxylmethyloxyphenyl)-1,3-dipropylxanthine (XAC) on heat production.
Figure 6B:
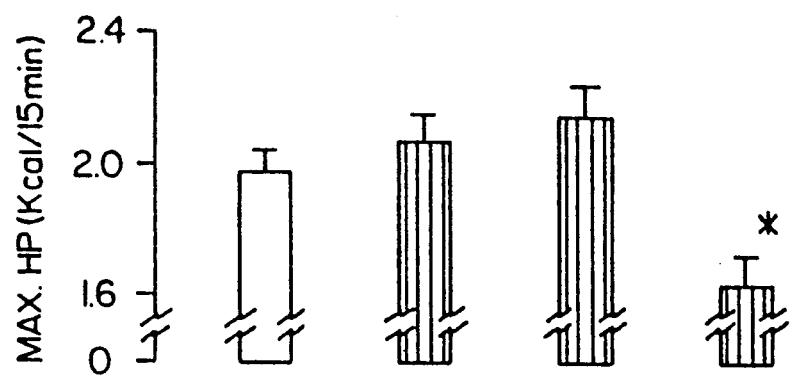
Figure 6C:
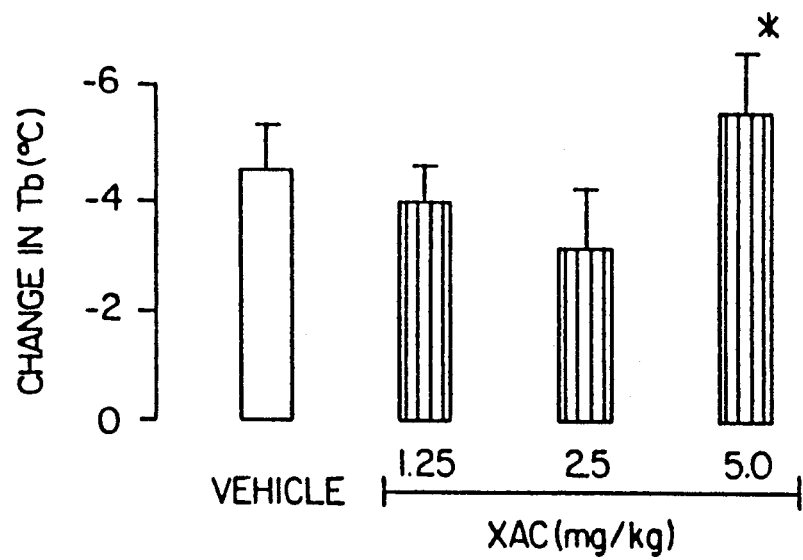

The results on XAC (FIGS. 6a-6c) are not as cleancut as those for the other compounds; the main reason being the solubility problem. However, XAC showed a 7% increase in maximum and total thermogenesis, very close to the 10% or more found in the other compounds which elicited statistically significant increases.

Figure 11A:
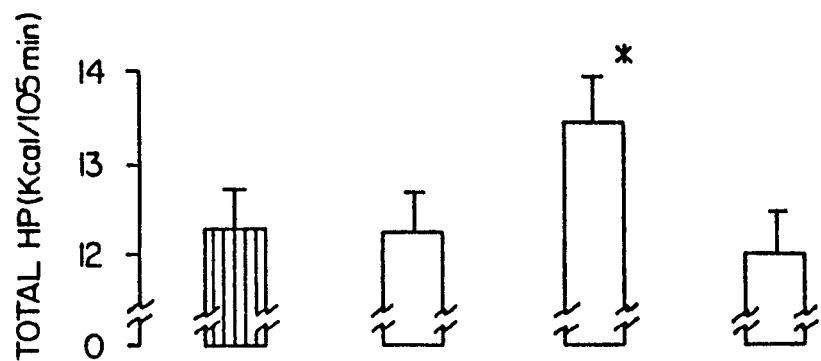
FIGS. 11a-11c are graphs which illustrate the effect of adenosine deaminase on heat production.
Figure 11B:
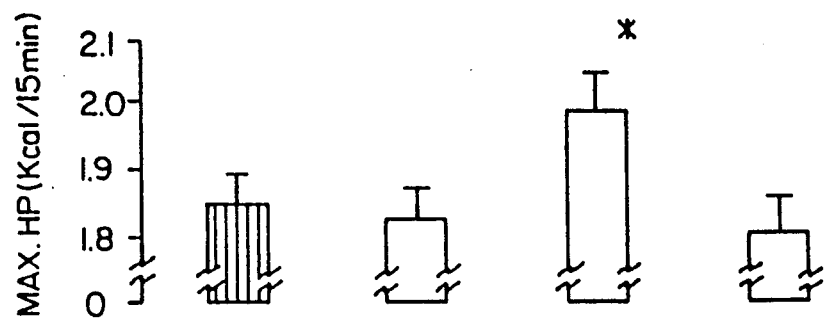
Figure 11C:
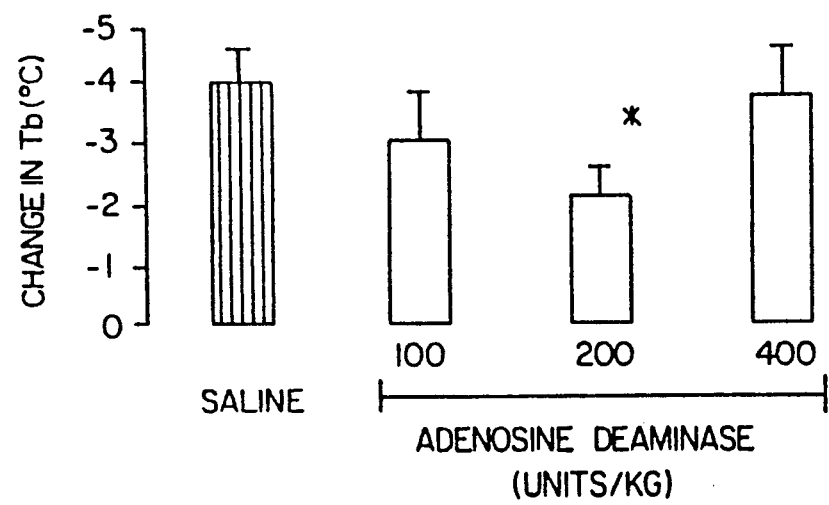

Since some of the xanthines (e.g. caffeine, theobromine) used also possess antiphosphodiesterase enzyme (PDE) activity, it is a possibility that the action of these xanthines may be through PDE inhibition rather than adenosine antagonism. To dispel this possibility, we have selected enprofylline (3-propylxanthine), which is known to have PDE inhibitory effect ($IC_{50}=100-400$ $\mu M$) but devoid of adenosine antagonism (Persson & Kjellin, Enprofylline, a principally new antiasmatic xanthine, Acta Pharmacol. Toxicol. 49:313-316, 1981) to test its influence on thermogenesis and cold resistance. The results indicated that enprofylline is without effect on stimulation of thermogenesis (FIGS. 9a-9c), confirming our contention that it is the antagonism of adenosine receptors but not the inhibition of PDE activity that is responsible for the beneficial effects of the many xanthines employed herein. To further demonstrate the validity of this claim, we used an adenosine de-activator which converts adenosine to other metabolizable compounds by chemical means. For example, adenosine deaminase, which converts exclusively adenosine to inosine and thereby eliminates the deleterious effects of adenosine in thermogenesis. As can be seen from FIGS. 11a-11c, pretreating the rats by injection with adenosine deaminase significantly increased heat production and cold tolerance. It is also contemplated that adenosine kinase, which phosphorylates adenosine to adenosine monophosphate (AMP), would have a similar effect in improving cold tolerance. Optionally, AMP may be further phosphorylated to adenosine diphosphate (ADP) and then to adenosine triphosphate (ATP) by nucleoside monophosphate kinase.

Figure 10A:
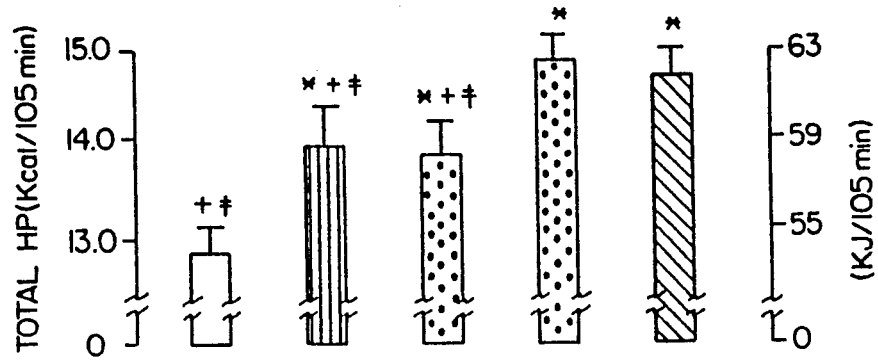
FIGS. 10a-10c are graphs which illustrate the effect of combined 8-PT and AMPY administration on heat production.
Figure 10B:
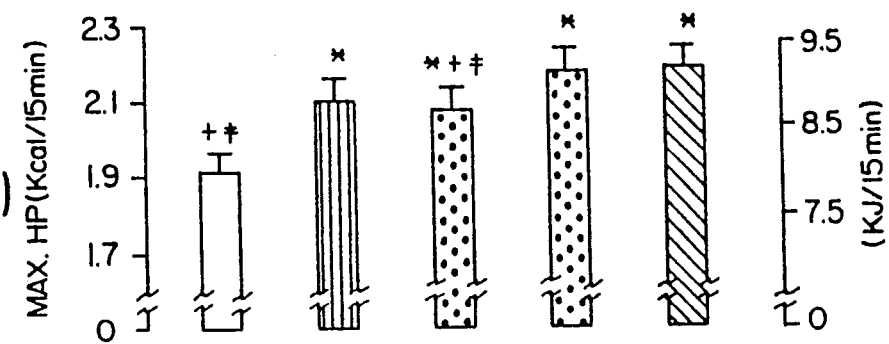
Figure 10C:
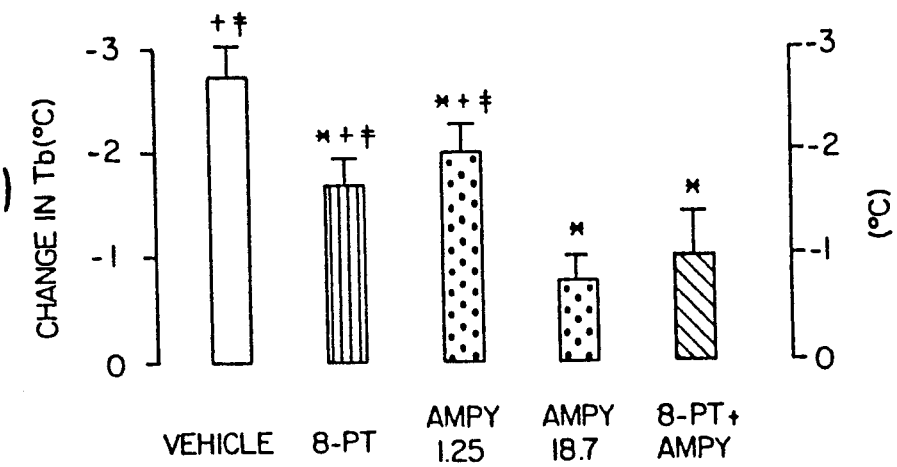

Our results also indicate that the maximum thermogenesis effect by optimal dose of 8-PT (5 mg/kg, i.p.) was significantly lower than that with the optimal dose of AMPY (18.7 mg/kg, i.p.) (FIG. 10). Applicant has found that the deficit could be eradicated by combining optimal 8-PT dose with a low dose of AMPY (1.25 mg/kg, i.p.). In fact, the thermogenic effect of 8-PT, when administered simultaneously with a low dose of AMPY (FIGS. 10a–10c), is markedly enhanced, and is increased to the same level as that after a high dose of AMPY. As the magnitude of HP induced by the combined drug treatment may have already reached the maximum aerobic capacity of the animal, it is difficult to distinguish whether these two compounds elicit thermogenesis in a synergistic or additive manner.

To demonstrate that a combination of adenosine antagonist and nutritional supplement is a better treatment than the use of adenosine antagonist or nutritional supplement alone, we have conducted experiments in rats verifying this prediction. Tables 1 and 2 below show that orally administered nutritional supplement alone, either in the form of different carbohydrate mixtures or as a mixture of carbohydrates, fat and protein, enhanced heat production and the magnitude and the duration of cold tolerance.

TABLE 1

EFFECTS OF CARBOHYDRATE FEEDING ON COLD TOLERANCE IN RATS#

| Treatment (n-8) | Total Hp (Kcal) | Max. Hp (Kcal/15 min) | Change in Tb (°C.) | Duration (min) |
| --- | --- | --- | --- | --- |
| Water 5 ml | 10.90 ± 0.91 | 1.50 ± 0.03 | −10.83 ± 0.76 | 144.4 ± 6.98 |
| Sucrose 52% aq. solution | 14.31 ± 1.27* (31%) | 1.66 ± 0.04* (10%) | −8.68 ± 0.69 | 163.1 ± 7.23* |
| Starch 55.2% aq. solution | 14.60 ± 0.98* (34%) | 1.59 ± 0.05 (6%) | −9.05 ± 1.11 | 166.9 ± 5.59* |
| Gl:Su:St (1:3:6.4) | 15.20 ± 0.98* (39%) | 1.64 ± 0.05* (9%) | −7.88 ± 0.64* | 172.5 ± 4.59* |
| Gl:Su:St (1:6:3.2) | 14.41 ± 0.76* (32%) | 1.58 ± 0.03 (5%) | −10.98 ± 0.89 | 170.6 ± 5.89* |
| Gl:Su:St (1:5:10.6) | 16.63 ± 0.96* (53%) | 1.67 ± 0.07* (11%) | −5.50 ± 0.96* | 177.5 ± 2.20* |
| Gl:Su:St (1:10:5.3) | 15.09 ± 1.78* (39%) | 1.68 ± 0.06* (11%) | −10.33 ± 0.97 | 170.0 ± 5.38* |

Feeding was by gastric tube in a volume of 5 ml 15 min prior to cold exposure.
*Significantly different from water control, $p < 0.05$ (Wilcoxin's Rank Test).
Numbers in brackets indicate percentage increase in heat production over control value.
Gl = Glucose; Su = Sucrose; St = Starch
The composition of carbohydrate is by weight ratio, wherein 1 = 0.26 g.
The carbohydrate mixtures are dissolved in water.

TABLE 2

EFFECTS OF SUBSTRATE FEEDING ON COLD TOLERANCE IN RATS#

| Treatment (n-9) | Total Hp (Kcal) | Max. Hp (Kcal/15 min) | Change in Tb (°C.) | Duration (min) |
| --- | --- | --- | --- | --- |
| Water 5 ml | 16.12 ± 0.94 | 1.67 ± 0.05 | −12.12 ± 0.75 | 177.2 ± 8.36 |
| Gl:Su:St (1:5:10.6) | 24.61 ± 1.28* (53%) | 1.90 ± 0.06* (14%) | −10.42 ± 1.13 | 231.7 ± 4.78* |
| Mixture (16 Kcal) | 25.83 ± 1.64* (60%) | 2.01 ± 0.07* (20%) | −8.52 ± 1.83* | 230.0 ± 4.08* |

Feeding was by gastric tube in a volume of 5 ml either 15 min (for Gl:Su:St) or 30 min (for mixture) prior to cold exposure.
*Significantly different from water control, p 0.05 (Wilcoxin's Rank Test). The composition of carbohydrate is by weight ratio.
Numbers in brackets indicate percentage increase in heat production over control value.
Gl = Glucose; Su = Sucrose; St = Starch
Composition of mixture = Gl:Su:St:Egg Albumin:Corn Oil - 1:3:6.4:5:0.33 (weight ratio, wherein 1 = 0.26 g).
The mixtures are dissolved in water.
Composition of mixture in terms of weight percentages, carbohydrate = 66.2%, fat = 1.9% and protein = 31.9%.

However, as illustrating in Table 3 below, the combination of a general adenosine antagonist, theobromine (administered orally in the form of cocoa powder plus water) and carbohydrate mixtures resulted in the greatest improvement of heat production and cold tolerance as compared to the treatment using water, cocoa, or nutritional supplment alone. Consequently, the decrease of body temperature (Tb) was the least and the duration of cold exposure was the longest in adenosine antagonist and nutritional supplement treatment. It is therefore likely that this combination is the best for improving cold resistance and based on Tables 2 and 3, theobromine plus a nutritional mixture including carbohydrates, protein and fat is a desirable formula.

TABLE 3

EFFECTS OF COCOA AND CARBOHYDRATE
FEEDING ON COLD TOLERANCE IN RATS

| Treatment (n-8) | Total HP (Kcal) | Max. HP (Kcal/15 min) | Change in Tb (°C.) | Duration (min) |
|---|---|---|---|---|
| Water 5 ml | 10.75 ± 0.59 | 1.42 ± 0.04 | −10.45 ± 0.62 | 140.6 ± 5.26 |
| Cocoa 1 g | 11.42 ± 0.72 (6%) | 1.59 ± 0.03* (12%) | −9.84 ± 0.46 | 144.4 ± 5.26 |
| Gl:Su:St (1:3:6.4) | 16.04 ± 0.68* (49%) | 1.61 ± 0.04* (13%) | −6.85 ± 1.26* | 176.3 ± 3.51* |
| Cocoa 1 g + Gl:Su:St 1:3:6.4) | 17.43 ± 0.64* (61%) | 1.72 ± 0.04* (21%) | −5.53 ± 0.87* | 180.0 ± 0.00* |
| Gl:Su:St (1:5:10.6) | 16.49 ± 0.67* (32%) | 1.67 ± 0.03 (5%) | −5.75 ± 1.12* | 176.3 ± 3.51* |
| Cocoa 1 g + Gl:Su:St (1:5:10.6) | 17.71 ± 0.86* (65%) | 1.77 ± 0.10* (25%) | −5.03 ± 1.16* | 180.0 ± 0.00* |

Feeding was by gastric tube in a volume of 5 ml 15 min prior to cold exposure. The composition is by weight ratio, wherein 1 = 0.26 g.
*Significantly different from water control, p < 0.05 (Wilcoxin's Rank Test).
+ Significantly different from cocoa control, p < 0.05 (Wilcoxin's Rank Test).
Numbers in brackets indicate percentage increase in heat production over water control group.
Gl = Glucose; Su = Sucrose; St = Starch
The mixtures are dissolved in water.

As seen in Tables 4 to 6 and FIGS. 12 to 16a-16b, initial experiments in humans of both sexes have shown that the combination of orally administered theobromine in amounts of 2 to 4 mg/kg of body weight and various combinations of nutritional supplements effective in improving cold tolerance and retarding the onset of hypothermia in severe cold.

Figure 12:
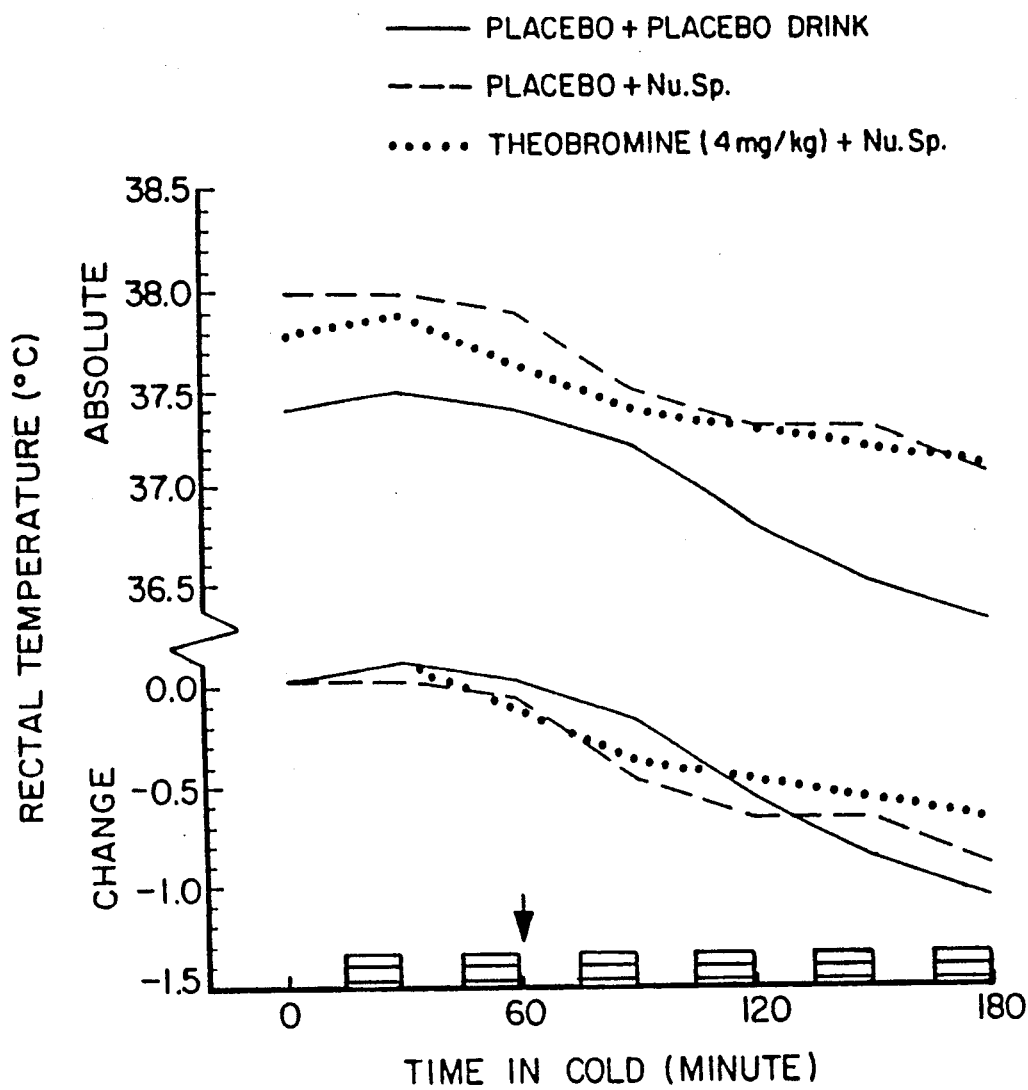
FIG. 12 is a graph which illustrates the effects of placebo treatments, nutritional supplement alone, and theobromine (4 mg/kg p.o.) plus nutritional supplement on cold tolerance in a female subject; experimental protocol as in Table 4.

With specific reference to FIG. 12, the hatched boxes indicate duration of walking on a motorized treadmill at 4 mile/hr. Arrow indicates time of ingestion of either placebo drink or nutritional supplement. Theobromine is taken orally at time 0.

Figure 13:
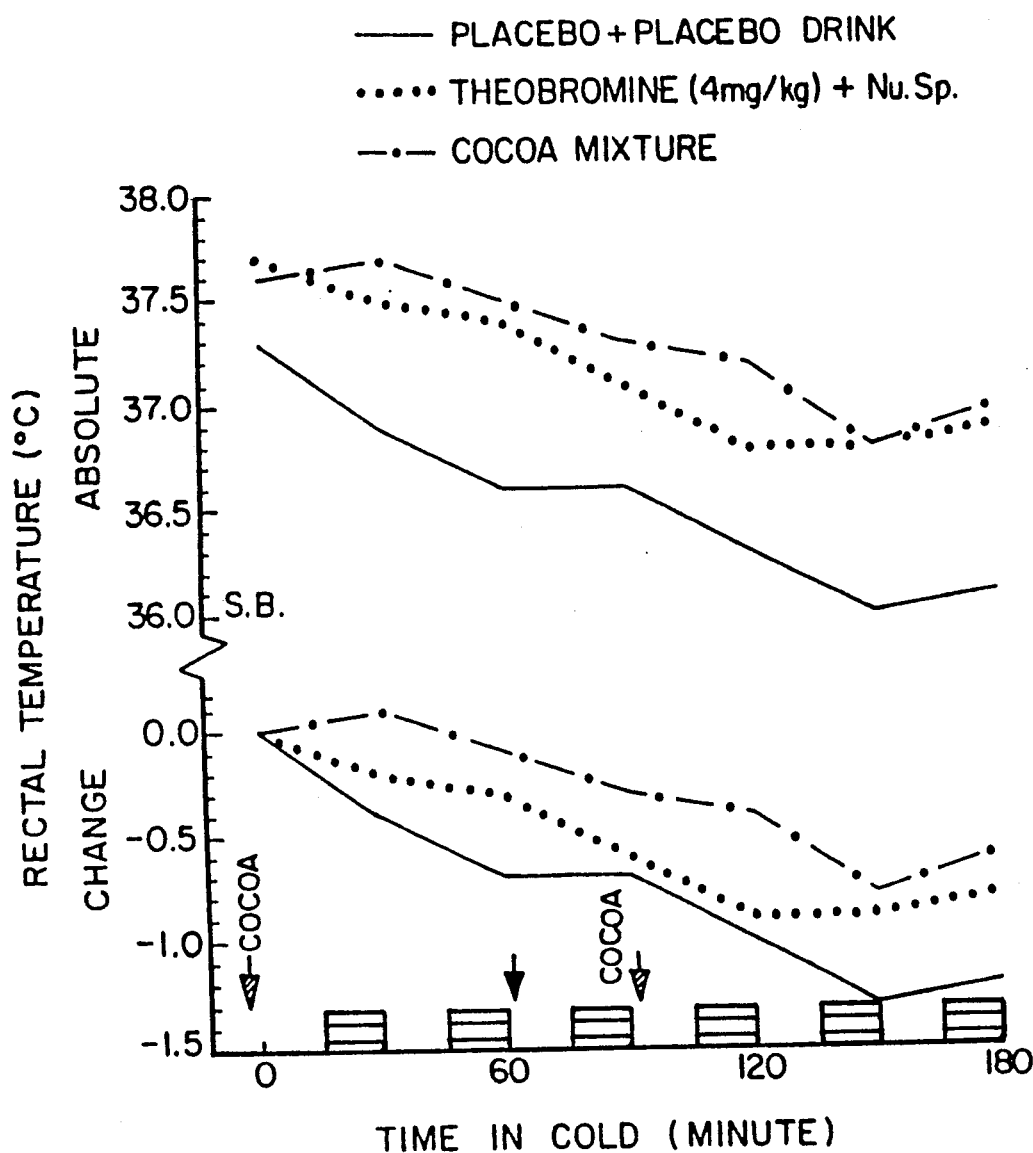
FIG. 13, is a graph which illustrates the effect of theobromine (4 mg/kg p.o.) and nutritional supplement on improving cold tolerance in a male subject; experimental protocol as in Table 4.

In FIG. 13, the hatched boxes indicate duration of walking on a motorized treadmill at 5 mile/hr. Arrow indicates time of ingestion of placebo drink and nutritional supplement. Arrows with cocoa on top indicate time of ingestion of cocoa plus nutritional supplement (total amount of theobromine in cocoa and nutritional supplement are equivalent to those in theobromine + nutritional supplement).

Figure 14:
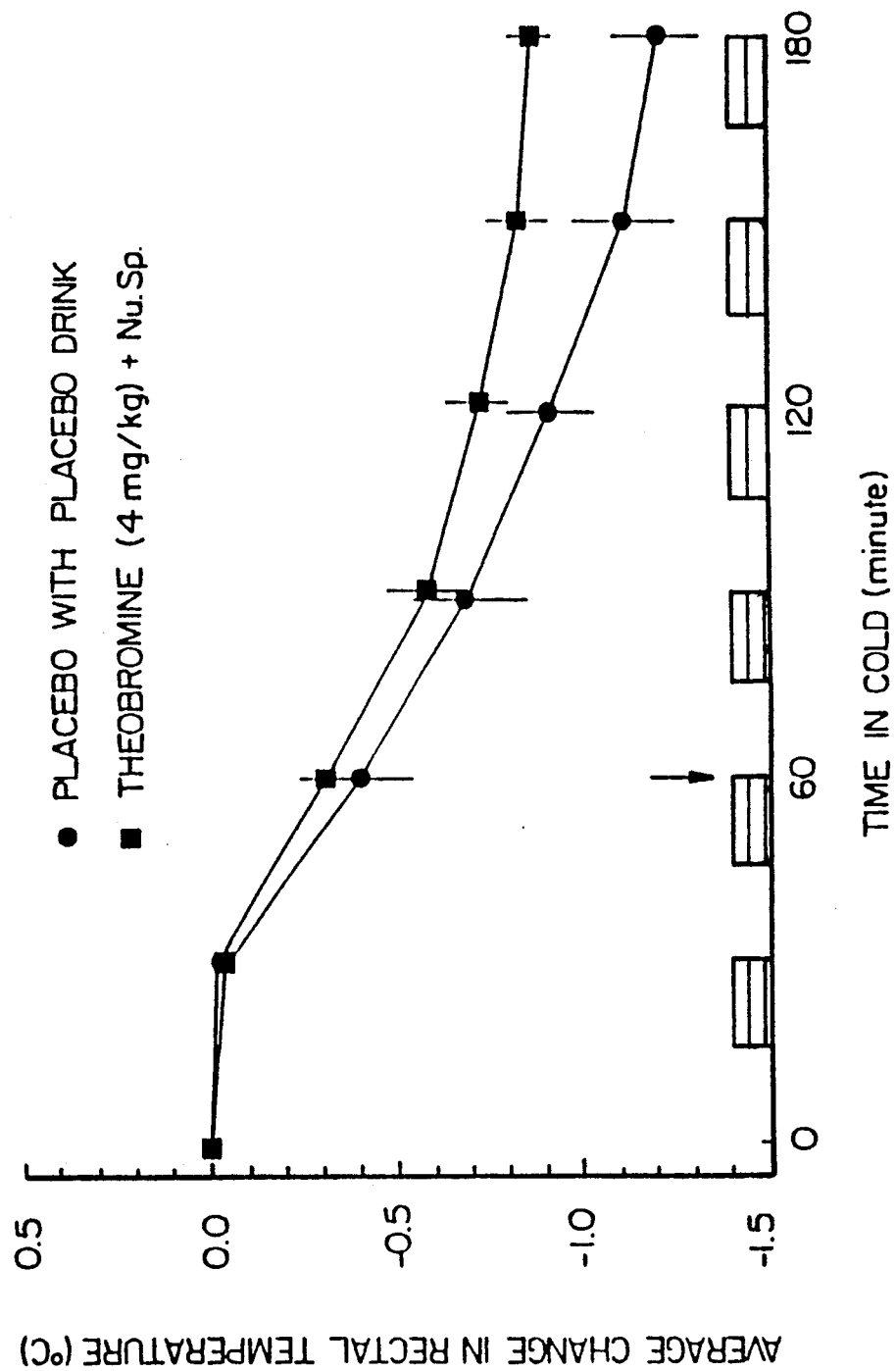
FIG. 14 is a graph which illustrates the benefit of a combination theobromine (4 mg/kg p.o.) and nutritional supplement on improving cold tolerance in humans (3 males, 2 females); experiment protocols as in Table 4.

In FIG. 14, the hatched boxes indicate duration of walking on a motorized treadmill at 4 or 5 miles/hr (5 for males, 4 for females). Arrow indicates time of ingesting placebo drink or nutritional supplement.

TABLE 4

Change in rectal temperature (°C.) in male (3) and female (2) subjects walking (4–5 miles/hour) intermittently (50% of time) at −10° C. for 3 hours dressed in shorts (males) or T-shirt and shorts (females).

CHANGE IN RECTAL TEMPERATURE

| | Subjects | | | | | |
|---|---|---|---|---|---|---|
| Time | M. B. | J. D. | S. B. | T. B. | B. M. | Average +/− se |
| Treatment - Placebo and Placebo | | | | | | |
| 0 | 0.00 | 0.00 | 0.00 | 0.00 | 0.00 | 0.000 +/− 0.000 |
| 30 | 0.10 | −0.10 | −0.40 | 0.20 | 0.00 | −0.040 +/− 0.092 |
| 60 | 0.00 | −0.80 | −0.70 | −0.10 | −0.40 | −0.400 +/− 0.141 |
| 90 | −0.20 | −1.10 | −0.70 | −0.40 | −1.10 | −0.700 +/− 0.162 |
| 120 | −0.60 | −1.10 | −1.00 | −0.60 | −1.30 | −0.920 +/− 0.125 |
| 150 | −0.90 | −1.10 | −1.30 | −0.70 | −1.60 | −1.120 +/− 0.140 |
| 180 | −1.10 | −1.15 | −1.20 | −0.90 | −1.70 | −1.210 +/− 0.119 |
| Treatment - Pure Theobromine (4 mg/kg) and Nutritional Supplement (Nu. Sp.) | | | | | | |
| 0 | 0.00 | 0.00 | 0.00 | 0.00 | 0.00 | 0.000 +/− 0.000 |
| 30 | 0.10 | −0.10 | −0.20 | 0.00 | 0.10 | −0.020 +/− 0.052 |
| 60 | −0.15 | −0.70 | −0.30 | −0.20 | −0.20 | −0.310 +/− 0.090 |
| 90 | −0.40 | −1.10 | −0.60 | −0.40 | −0.40 | −0.580 +/− 0.121 |
| 120 | −0.50 | −1.10 | −0.90 | −0.50 | −0.60 | −0.720 +/− 0.107 |
| 150 | −0.60 | −1.20 | −0.90 | −0.60 | −0.85 | −0.830 +/− 0.100 |
| 180 | −0.70 | −1.20 | −0.80 | −0.70 | −0.95 | −0.870 +/− 0.084 |

Nu. Sp.

%/w  355 KCal (1480 KJ)
16.2  13.0 g Protein (casein and soya protein isolates)
24.5  19.6 g Fat (corn oil and triglycerides)
59.2  47.3 g Carbohydrate (corn syrup solids and sucrose)
     in 235 ml aq. solution

TABLE 5

Change in rectal temperature (°C.) in male (2) walking (5 miles/hour) intermittently (50% of time) at −10° C. for 3 hours dressed in shorts.

CHANGE IN RECTAL TEMPERATURE

| | Subjects | |
|---|---|---|
| Time | J. D. | S. B. |
| Treatment - Placebo and Placebo | | |
| 0 | 0.00 | 0.00 |
| 30 | 0.05 | −0.40 |
| 60 | −0.45 | −0.70 |

TABLE 5-continued

| | | |
|---|---|---|
| 90 | −0.85 | −0.70 |
| 120 | −1.00 | −1.00 |
| 150 | −1.05 | −1.10 |
| 180 | −1.10 | −1.20 |
| Treatment - 2 mg/kg Theobromine and Nu. Sp. | | |
| 0 | 0.00 | 0.00 |
| 30 | 0.00 | 0.10 |
| 60 | −0.40 | −0.20 |
| 90 | −0.85 | −0.55 |
| 120 | −0.90 | −0.70 |
| 150 | −0.90 | −0.70 |
| 180 | −0.90 | −0.70 |

Nu. Sp. = Nutritional Supplement (same as in Table 4)

| %/w | 355 KCal (1480 KJ) |
|---|---|
| 16.2 | 13.0 g Protein |
| 24.5 | 19.6 g Fat |
| 59.2 | 47.3 g Carbohydrate |
| | in 235 ml aq. solution |

TABLE 6

Change in rectal temperature (°C) in male (1) and female (1) subjects walking (4–5 miles/hour) intermittently (30% of time) at −10° C. for 3 hours in shorts (males) or T-shirt and shorts (females).

CHANGE IN RECTAL TEMPERATURE

| | Subjects | |
|---|---|---|
| Time | A. B. | M. B. |
| Treatment - Placebo and Placebo | | |
| 0 | 0.00 | 0.00 |
| 30 | −0.40 | −0.15 |
| 60 | −0.95 | −0.50 |
| 90 | −1.25 | −0.80 |
| 120 | −1.50 | −1.05 |
| 150 | −1.65 | −1.20 |
| 180 | ** | −1.40 |
| Treatment - CHOP 2 mg/kg Theobromine via Cocoa. | | |
| 0 | 0.00 | 0.00 |
| 30 | −0.50 | 0.00 |
| 60 | −0.65 | −0.30 |
| 90 | −0.75 | −0.50 |
| 120 | −0.85 | −0.80 |
| 150 | −0.95 | −0.90 |
| 180 | −0.90 | −1.00 |

CHOP = Carbohydrate Protein Supplement

| %/w | 250 KCal (1042 KJ) |
|---|---|
| 46.2 | 30.0 g Casein (calcium caseinate) |
| 5.2 | 3.4 g Glucose |
| 15.5 | 10.1 g Sucrose |
| 33.1 | 21.5 g Corn Starch |
| | 9.0 g Cocoa (containing 1.5%/w Theobromine) in 235 ml aq. solution. |

**Individual removed from cold due to reaching maximum allowable decrease in body temperature.

The embodiments of the invention in which an exclusive property or privilege is claimed are defined as follows:

1. An orally ingestible composition for improving the cold tolerance of animals and humans which consists essentially of:
   (a) an adenosine receptor antagonist in an amount effective to improve the cold tolerance of said animals, said antagonist selected from the group of caffeine, theobromine, 8-phenyltheophylline, 8-cyclopentyltheophylline, 8-(4-(2-aminoethyl-)amino carboxymethyloxyphenyl)-1,3-dipropylxanthine 8-(amino-4-chlorophenyl)-1,3-dipropylxanthine 8-(p-sulfophenyl)-1,3-dipropylxanthine, alone or mixed with two or more thereof, or in combination with theophylline or aminophylline or both; and
   (b) a nutritionally effective and cold tolerance improving amount of a nutritional supplement consisting of a mixture of 47 to 66% by weight of carbohydrate, 15 to 50% by weight of protein and 0 to 25% by weight of fat.

2. The composition according to claim 1, wherein the carbohydrate in the nutritional supplement mixture contains glucose, sucrose and starch in a weight ratio of about 1:3:6 to about 1:10:10.

3. A composition according to claim 1, wherein the mixture of carbohydrate, fat and protein comprises about 59.2%/w of carbohydrate, about 24.5%/w of fat and about 16.2%/w of protein.

4. A composition according to claim 1, wherein the adenosine receptor antagonist is theobromine.

5. A composition according to claim 4, wherein the protein is egg albumin.

6. A composition according to claim 1, for improving the cold tolerance of humans which includes as adenosine receptor antagonist theobromine in unit dosage form of about 2 to 4 mg/kg of body weight.

7. A composition according to claim 6, wherein the theobromine is in the form of cocoa powder containing 1–2%/w of theobromine.

8. A composition according to claim 1, wherein the nutritional supplement is a mixture of 50–60%/w of carbohydrate, 15–50%/w of protein and −25%/w of fat.

9. A composition according to claim 1, wherein the carbohydrate is a mixture of glucose, sucrose and corn starch.

10. A composition according to claim 9, wherein the protein is casein.

11. A composition according to claim 10, wherein the mixture of carbohydrate and protein comprises, about 53.8%/w of carbohydrate, 0%/w of fat and about 46.2%/w of protein.

* * * * *